(12) United States Patent
Wenzel et al.

(10) Patent No.: US 8,480,852 B2
(45) Date of Patent: *Jul. 9, 2013

(54) COOLING SUBSTRATES WITH HYDROPHILIC CONTAINMENT LAYER AND METHOD OF MAKING

(75) Inventors: Scott W. Wenzel, Neenah, WI (US); Jeffery Richard Seidling, Appleton, WI (US); Helen Kathleen Moen, Hortonville, WI (US); Frederick John Lang, Neenah, WI (US); Stephanie Diana Scharenbroch, Neenah, WI (US); Mark Anthony Barnes, Neenah, WI (US); Judy Marie Casper, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 292 days.

This patent is subject to a terminal disclaimer.

(21) Appl. No.: 12/622,581

(22) Filed: Nov. 20, 2009

(65) Prior Publication Data

US 2011/0123578 A1    May 26, 2011

(51) Int. Cl.
*D21H 27/32* (2006.01)
*D21H 19/12* (2006.01)
*D21H 19/14* (2006.01)
*D21H 19/20* (2006.01)
*A61K 8/02* (2006.01)
*A61K 8/31* (2006.01)
*A61K 8/37* (2006.01)

(52) U.S. Cl.
USPC ........ 162/124; 162/135; 162/158; 162/164.1; 162/172; 162/179; 162/185; 424/402; 428/172; 428/195.1

(58) Field of Classification Search
USPC ........... 162/109, 123–133, 158, 164.1, 168.1, 162/172–173, 175, 179, 184; 424/400–402, 424/414; 428/172, 195.1
See application file for complete search history.

(56) References Cited

U.S. PATENT DOCUMENTS

| | | | |
|---|---|---|---|
| 1,253,603 | A | 1/1918 | Keagy |
| 1,579,124 | A | 3/1926 | MacGrath |

(Continued)

FOREIGN PATENT DOCUMENTS

| | | |
|---|---|---|
| BE | 0 905 997 A | 4/1987 |
| EP | 1 078 980 A1 | 2/2001 |

(Continued)

OTHER PUBLICATIONS

Tappi Official Test Method T 411 om-89, "Thickness (Caliper) of Paper, Paperboard, and Combined Board," published by the TAPPI Press, Atlanta, Georgia, revised 1989, pp. 1-3.

(Continued)

*Primary Examiner* — Jose A Fortuna
(74) *Attorney, Agent, or Firm* — H. Michael Kubicki (57) ABSTRACT

Wiping products, such as facial tissues, contain an interior temperature change composition and an exterior hydrophilic lotion composition that can provide a cooling sensation when contacted with the skin of a user. The temperature change composition, for instance, can contain one or more phase change agents that undergo a phase change at slightly elevated temperatures. The phase change agents, in one embodiment, can have a relatively high heat of fusion. When undergoing a phase change, the phase change agents absorb heat and thereby provide a cooling feeling to the skin of a user. The hydrophilic lotion composition may contain a carrier and a thermo-reversible gelling agent. The hydrophilic lotion composition maintains the temperature change composition within the tissue and helps to prevent skin irritation.

11 Claims, 2 Drawing Sheets

U.S. PATENT DOCUMENTS

| | | | |
|---|---|---|---|
| 1,885,278 A | 11/1932 | Monett | |
| 2,721,554 A * | 10/1955 | Joa | 604/382 |
| 3,264,172 A | 8/1966 | Regutti | |
| 3,301,746 A | 1/1967 | Sanford et al. | |
| 3,516,941 A | 6/1970 | Matson | |
| 3,585,104 A | 6/1971 | Kleinert | |
| 3,607,348 A | 9/1971 | Wray et al. | |
| 3,812,000 A | 5/1974 | Salvucci, Jr. et al. | |
| 3,974,025 A | 8/1976 | Ayers | |
| 4,100,324 A | 7/1978 | Anderson et al. | |
| 4,191,609 A | 3/1980 | Trokhan | |
| 4,208,459 A | 6/1980 | Becker et al. | |
| 4,504,442 A | 3/1985 | Rosenblatt et al. | |
| 4,514,345 A | 4/1985 | Johnson et al. | |
| 4,528,239 A | 7/1985 | Trokhan | |
| 4,585,482 A | 4/1986 | Tice et al. | |
| 4,594,130 A | 6/1986 | Chang et al. | |
| 4,604,313 A | 8/1986 | McFarland et al. | |
| 4,637,859 A | 1/1987 | Trokhan | |
| 4,793,898 A | 12/1988 | Laamanen et al. | |
| 4,985,064 A | 1/1991 | Redlich et al. | |
| 5,098,522 A | 3/1992 | Smurkoski et al. | |
| 5,126,070 A | 6/1992 | Leifheit et al. | |
| 5,275,700 A | 1/1994 | Trokhan | |
| 5,328,565 A | 7/1994 | Rasch et al. | |
| 5,350,624 A | 9/1994 | Georger et al. | |
| 5,496,624 A | 3/1996 | Stelljes, Jr. et al. | |
| 5,525,345 A * | 6/1996 | Warner et al. | 424/402 |
| 5,529,665 A | 6/1996 | Kaun | |
| 5,554,467 A | 9/1996 | Trokhan et al. | |
| 5,566,724 A | 10/1996 | Trokhan et al. | |
| 5,595,628 A | 1/1997 | Gordon et al. | |
| 5,624,676 A * | 4/1997 | Mackey et al. | 424/414 |
| 5,628,876 A | 5/1997 | Ayers et al. | |
| 5,650,218 A | 7/1997 | Krzysik et al. | |
| 5,705,164 A * | 1/1998 | Mackey et al. | 424/400 |
| 5,716,692 A * | 2/1998 | Warner et al. | 428/153 |
| 5,830,487 A * | 11/1998 | Klofta et al. | 424/402 |
| 5,840,671 A | 11/1998 | Fujimura et al. | |
| 5,869,075 A * | 2/1999 | Krzysik | 424/414 |
| 6,028,018 A | 2/2000 | Amundson et al. | |
| 6,187,695 B1 | 2/2001 | Krzysik et al. | |
| 6,238,682 B1 * | 5/2001 | Klofta et al. | 424/402 |
| 6,258,249 B1 | 7/2001 | Simpson | |
| 6,428,794 B1 | 8/2002 | Klofta et al. | |
| 6,432,270 B1 | 8/2002 | Liu et al. | |
| 6,582,558 B1 | 6/2003 | Liu | |
| 6,733,773 B1 * | 5/2004 | Hsu et al. | 424/443 |
| 6,749,860 B2 | 6/2004 | Tyrrell et al. | |
| 6,756,520 B1 * | 6/2004 | Krzysik et al. | 604/360 |
| 6,825,393 B2 * | 11/2004 | Roe et al. | 604/364 |
| 6,855,410 B2 * | 2/2005 | Buckley | 428/311.11 |
| 6,860,967 B2 | 3/2005 | Baumoller et al. | |
| 6,896,766 B2 | 5/2005 | Sarbo et al. | |
| 6,905,697 B2 * | 6/2005 | Baumoller et al. | 424/402 |
| 6,949,167 B2 | 9/2005 | Shannon et al. | |
| 7,005,557 B2 | 2/2006 | Klofta et al. | |
| 7,008,507 B2 | 3/2006 | Urlaub et al. | |
| 7,115,273 B2 * | 10/2006 | Shanklin et al. | 424/404 |
| 7,169,400 B2 * | 1/2007 | Luu et al. | 424/400 |
| 7,300,547 B2 | 11/2007 | Luu et al. | |
| 7,361,361 B2 | 4/2008 | Luu et al. | |
| 7,381,693 B2 * | 6/2008 | Keenan et al. | 510/141 |
| 7,485,373 B2 | 2/2009 | Krzysik et al. | |
| 7,582,577 B2 | 9/2009 | Vinson | |
| 8,012,495 B2 * | 9/2011 | Luu et al. | 424/400 |
| 2002/0051823 A1 | 5/2002 | Yan et al. | |
| 2002/0192552 A1 | 12/2002 | Lampe-Onnerud et al. | |
| 2003/0077962 A1 | 4/2003 | Krzysik et al. | |
| 2003/0108761 A1 | 6/2003 | Eddlemon | |
| 2003/0133832 A1 | 7/2003 | D'Ottone | |
| 2003/0147773 A1 | 8/2003 | Bryner et al. | |
| 2003/0174810 A1 | 9/2003 | Korenev et al. | |
| 2003/0188841 A1 | 10/2003 | Buder et al. | |
| 2003/0230492 A1 | 12/2003 | Kadlec et al. | |
| 2004/0009223 A1 | 1/2004 | Garg et al. | |
| 2004/0076544 A1 | 4/2004 | Dao | |
| 2004/0140347 A1 | 7/2004 | Mihaylov et al. | |
| 2004/0234561 A1 | 11/2004 | Ansmann et al. | |
| 2005/0058674 A1 | 3/2005 | Joseph et al. | |
| 2005/0058693 A1 | 3/2005 | Joseph et al. | |
| 2005/0100573 A1 * | 5/2005 | Baumoller et al. | 424/402 |
| 2005/0136765 A1 | 6/2005 | Shannon | |
| 2005/0238701 A1 | 10/2005 | Kleinwaechter | |
| 2005/0250402 A1 | 11/2005 | Wild et al. | |
| 2005/0274470 A1 | 12/2005 | Shannon et al. | |
| 2005/0277568 A1 * | 12/2005 | Keenan et al. | 510/438 |
| 2006/0110432 A1 * | 5/2006 | Luu et al. | 424/443 |
| 2006/0147502 A1 | 7/2006 | Koenig et al. | |
| 2007/0087041 A1 * | 4/2007 | Luu et al. | 424/443 |
| 2007/0148447 A1 | 6/2007 | Amundson et al. | |
| 2007/0148448 A1 | 6/2007 | Joseph et al. | |
| 2008/0045913 A1 | 2/2008 | Johnson et al. | |
| 2008/0085290 A1 * | 4/2008 | Flugge-Berendes et al. | 424/401 |
| 2008/0107698 A1 * | 5/2008 | Luu et al. | 424/404 |
| 2008/0188560 A1 | 8/2008 | Mohammadi et al. | |
| 2009/0110656 A1 | 4/2009 | Lemke et al. | |
| 2009/0155325 A1 | 6/2009 | Wenzel et al. | |
| 2009/0157153 A1 * | 6/2009 | Lemke et al. | 607/114 |
| 2009/0191285 A1 * | 7/2009 | Howe et al. | 424/719 |
| 2009/0297586 A1 | 12/2009 | Shannon et al. | |
| 2010/0150989 A1 * | 6/2010 | Hoffman et al. | 424/445 |
| 2010/0266794 A1 * | 10/2010 | Wright et al. | 428/35.7 |
| 2011/0086084 A1 * | 4/2011 | Koenig et al. | 424/443 |
| 2011/0086085 A1 * | 4/2011 | Wenzel et al. | 424/443 |
| 2011/0123578 A1 * | 5/2011 | Wenzel et al. | 424/401 |
| 2011/0123584 A1 | 5/2011 | Seidling et al. | |
| 2011/0124769 A1 | 5/2011 | Moen et al. | |
| 2011/0303374 A1 * | 12/2011 | Chan et al. | 162/112 |

FOREIGN PATENT DOCUMENTS

| | | | |
|---|---|---|---|
| EP | 1 236 827 A1 | | 9/2002 |
| GB | 0 004 796 A | | 7/1914 |
| GB | 0 016 501 A | | 8/1916 |
| GB | 0 107 922 A | | 7/1917 |
| JP | 63-296758 A | | 12/1988 |
| JP | 02-127595 A | | 5/1990 |
| JP | 09-276027 A | | 10/1997 |
| JP | 2000-163629 A | | 6/2000 |
| JP | 2001-043447 A | | 2/2001 |
| JP | 2001-192306 A | | 7/2001 |
| JP | 2001-514552 A | | 9/2001 |
| WO | WO 9516824 A1 * | | 6/1995 |
| WO | WO 99/08555 A1 | | 2/1999 |
| WO | WO 99/42658 A1 | | 8/1999 |
| WO | WO 00/66835 A1 | | 11/2000 |
| WO | WO 03/035238 A2 | | 5/2003 |
| WO | WO 2006007564 A1 * | | 1/2006 |
| WO | WO 2009144596 A1 * | | 12/2009 |

OTHER PUBLICATIONS

Avato, P. et al., "Allylsulfide Constituents of Garlic Volatile Oil As Antimicrobial Agents," *Phytomedicine*, vol. 7, No. 3, 2000, pp. 239-243.

Baysan, A. et al., "Antimicrobial Effect of a Novel Ozone-Generating Device on Micro-Organisms Associated With Primary Root Carious Lesions In Vitro," *Journal of the European Organisation for Caries Research (ORCA)*, vol. 34, No. 6, Nov.-Dec. 2000, pp. 498-501.

Cosentino, S. et al., "In-Vitro Antimicrobial Activity and Chemical Composition of Sardinian *Thymus* Essential Oils," *Letters in Applied Microbiology*, vol. 29(2), 1999, pp. 130-135.

Demirci, Fatih et al., "Antimicrobial Activities of *Ferulago* Essential Oils," *Zeitschrift fur Naturforschung C*, vol. 55, No. 11-12, Nov.-Dec. 2000, pp. 886-889.

Djupesland, Per G. et al., "Nitric Oxide in the Nasal Airway: A New Dimension in Otorhinolaryngology," *American Journal of Otorhinolaryngology—Head and Neck Medicine and Surgery*, vol. 22, No. 1, Jan.-Feb. 2001, pp. 19-32.

Ender, Peter, "Contaminated Currency: The True Return on the Dollar," Wright-Patterson AFB Medical Center, *101st General Meeting of the American Society for Microbiology*, Orlando, FL, May 20-24, 2001, Session 220/C, Paper C-332.

Flamini, Guido et al., "Antimicrobial Activity of the Essential Oil of *Calamintha nepeta* and its Constituent Pulegone Against Bacteria and Fungi," *Phytotherapy Research*, vol. 13, No. 4, 1999, pp. 349-351.

Inoue, T. et al., "Solid-Liquid Phase Behavior of Binary Fatty Acid Mixtures 3. Mixtures of Oleic Acid With Capric Acid (Decanoic Acid) and Caprylic Acid (Octanoic Acid)," Chemistry and Physics of Lipids, vol. 132, 2004, pp. 225-234.

Karatzas A.K. et al., "The Combined Action of Carvacrol and High Hydrostatic Pressure on *Listeria monocytogenes* Scott A," *Journal of Applied Microbiology*, vol. 90, No. 3, 2001, pp. 463-469.

Kulevanova, S. et al., "Investigation of Antimicrobial Activity of Essential Oils of Several Macedonian *Thymus* L. Species (*Lamiaceae*)," *Bollettino Chimico Farmaceutico*, vol. 139, No. 6, Nov.-Dec. 2000, pp. 276-280.

Liu, Wai-Kin et al., "Mechanisms of the Bactericidal Activity of Low Amperage Electric Current (DC)," *Journal of Antimicrobial Chemotherapy*, vol. 39, No. 6, 1997, pp. 687-695.

Marcinkiewicz, Janusz, "Nitric Oxide and Antimicrobial Activity of Reactive Oxygen Intermediates," *Immunopharmacology*, vol. 37, No. 1, Aug. 1997, pp. 35-41.

Messick, Chad R. et al., "In-Vitro Activity of Polyhexamethylene Biguanide (PHMB) Against Fungal Isolates Associated With Infective Keratitis," The Journal of Antimicrobial Chemotherapy, vol. 44, 1999, pp. 297-298.

Ruberto, Giuseppe et al., "Antioxidant and Antimicrobial Activity of *Foeniculum vulgare* and *Crithmum maritimum*, Essential Oils," *Planta Medica*, vol. 66, No. 8, Dec. 2000, pp. 687-693.

Smith, Anthony W. et al., "Nitric Oxide-Induced Potentiation of the Killing of *Burkholderia cepacia* by Reactive Oxygen Species: Implications for Cystic Fibrosis," *The Journal of Medical Microbiology*, vol. 48, No. 5, May 1999, pp. 419-423.

Wang, Hai-Hong et al., "Inhibition of *Escherichia coli* by Dimethyl Fumarate," *International Journal of Food Microbiology*, vol. 65, Nos. 1-2, 2001, pp. 125-130.

Webert, Kathryn E. et al., "Effects of Inhaled Nitric Oxide in a Rat Model of *Pseudomonas aeruginosa* Pneumonia," *Critical Care Medicine*, vol. 28, No. 7, Jul. 2000, pp. 2397-2405.

\* cited by examiner

COOLING SUBSTRATES WITH HYDROPHILIC CONTAINMENT LAYER AND METHOD OF MAKING

BACKGROUND

Numerous healthcare and cosmetic products are applied to the skin in order to provide various benefits. Such products can include, for instance, lotions, creams, moisturizers, and the like. In some circumstances, the products are intended to provide a cooling feeling or cooling sensation to the skin once applied. Existing products typically provide skin cooling by combining skin cooling agents with other substances.

There are several different means to impart a cooling sensation to the skin, including using evaporation, neurosensory components, or physical agents such as phase change agents. One example of a cooling agent is menthol which provides cooling in the form of a physiological or neurosensory effect on nerve endings in the human body that sense temperature. The cooling sensation from menthol is not due to latent heat of evaporation but appears to be the result of direct stimulus on the cold receptors at the nerve endings.

The use of phase change agents to impart cooling is discussed, for instance, in PCT International Publication No. WO 2006/007564 entitled "Cosmetic Compositions and Methods for Sensory Cooling", which is incorporated herein by reference. In the '564 application, a skincare cosmetic composition is described in the form of a lotion that is intended for use in after-sun products, after-shave products, and body moisturizing products. The lotion is intended to create a cooling sensation on the skin by incorporating into the lotion components that absorb heat from the skin. In particular, ingredients are incorporated into the lotion that absorb heat from the skin and melt. The components have a relatively high heat of fusion which is defined in the '564 application as the heat absorbed by unit of mass of a solid chemical element at its melting point in order to convert the solid into a liquid at the same temperature. The '564 application states that the relatively high heat of fusion facilitates the absorption of heat from the skin to aid in melting the solid ingredient when applied to the skin, thereby cooling the skin temperature.

The use of phase change agents to impart cooling in tissues is disclosed, for instance, in PCT Patent Application No. PCT/IB2009/051515 entitled "Tissue Products having a Cooling Sensation When Contacted with Skin", which is incorporated herein by reference. The '515 application discloses the use of a phase change agent between multiple layers of a dry tissue web with a separate hydrophobic lotion layer on the exterior surfaces of the tissue product to provide a cooling sensation. This approach is problematic since components of the hydrophobic lotion can migrate into the hydrophobic phase change agent and disrupt its ability to cool. Alternatively, the phase change agent can migrate into the lotion on the exterior of the tissue and can cause skin irritation during use.

Therefore, a need exists for a means to effectively hold a phase change agent on or within a substrate, such as a tissue, such that it will cool the skin without allowing irritation to the skin. There also exists a need for a substrate, such as a tissue containing the composition, such that the composition can be delivered to the nose to moisturize, cool and soothe irritated noses, while holding this phase change agent within the substrate, keeping it from irritating skin. Additionally, there exists a need to effectively coat substrates such that the phase change agent is held on the interior of the tissue for extended periods of time. The need remains for a cooling tissue that is non-irritating during use.

SUMMARY

Generally, dry wiping products and particularly dry substrates that, when held against the skin, can provide a cooling sensation are disclosed herein. In one embodiment, for instance, the substrate can contain a facial tissue. The facial tissue can be used to provide comfort to a user's nose. For example, when suffering from the common cold, a person's nose can become inflamed and sore. In one embodiment, the present disclosure is directed to a tissue product that can not only be used to wipe one's nose, but can also provide the nose with a cooling sensation giving comfort and relief without causing skin irritation.

The present disclosure is directed to a temperature change composition for cooling the skin during use of the product in combination with a separate hydrophilic lotion layer on the exterior surfaces of the product. The operative temperature change composition contains an effective amount of at least one phase change agent. The temperature change composition may be incorporated into the tissue product in a manner so that substantially none of the temperature change composition is present on the exterior surfaces. The hydrophilic lotion layer helps to minimize the phase change agents from substantially coming in contact with the skin and/or transferring to the skin and causing irritation or being removed from the product prior to use.

The phase change agent incorporated into the temperature change composition can vary depending upon the particular application and the desired result. The phase change agent, for instance, can contain an oil soluble and hydrophobic material. Examples of phase change agents include hydrocarbons, waxes, oils, natural butters, fatty acids, fatty acid esters, dibasic acids, dibasic esters, 1-halides, primary alcohols, aromatic compounds, anhydrides, ethylene carbonates, polyhydric alcohols, and mixtures thereof. In one embodiment, for instance, a plurality of phase change agents can be incorporated into the temperature change composition. Particular examples of phase change agents may include tricaprin, parrafin, nonadecane, octadecane, stearyl heptanoate, lauryl lactate, lauryl alcohol, capric acid, caprylic acid, cetyl babassuate, mangifera indica (mango) seed butter, theobroma cacao (cocoa) seed butter, butyrospermum parkii butter, Di-$C_{12\text{-}15}$ Alkyl Fumarate, stearyl caprylate, cetyl lactate, cetyl acetate, $C_{24\text{-}28}$ alkyl methicone, glyceryl dilaurate, stearamidopropyl PG-dimonium chloride phosphate, jojoba esters, and combinations thereof.

Carriers for use in the hydrophilic lotion composition may include, but are not limited to, water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof. Desirably, the carrier is propylene glycol.

Typically, the hydrophilic lotion composition contains a carrier in an amount from about 1% by weight of the hydrophilic lotion composition to about 99.9% by weight of the hydrophilic lotion composition, more typically from about 2% by weight of the hydrophilic lotion composition to about 95% by weight of the hydrophilic lotion composition, and more typically from about 5% by weight of the hydrophilic lotion composition to about 90% by weight of the hydrophilic lotion composition.

Thermo-reversible gelling agents for use in the hydrophilic lotion composition may include, but are not limited to, salts of fatty acids such as sodium stearate, sodium palmitate, potassium stearate, hydroxystearic acid, polyethylene glycols and derivatives such as PEG-20, PEG-150 disteaurate, PEG-150 pentaerythrityl tetrastearate, disteareth-75 IPDI, disteareth-100 IPDI, fatty alcohols such as cetyl alcohol, fatty acids such as stearic acid, and combinations thereof. In addition, the thermo-reversible gelling agents may be formed by including an acid (i.e. stearic acid) and neutralizing it within the hydrophilic lotion composition with a base (i.e. sodium hydroxide) to make salts of fatty acids.

Using a thermo-reversible gelling agent is very important. A temperature change composition formed with a thermo-reversible gelling agent allows the product to be exposed to extreme temperatures during transportation of the product and still work effectively in the home when used by a consumer. The thermally reversible temperature change composition disclosed herein will change from a solid state to liquid state and back to a solid as the temperatures change. Thus, the phase change materials that provide a cooling effect are still available after long periods of storage and transportation at various temperatures. Previous temperature change composition, disclosed in for example, PCT Patent Application No. PCT/IB2009/051515 entitled "Tissue Products having a Cooling Sensation When Contacted with Skin" are not thermally reversible and do not provide these benefits.

Typically, the hydrophilic lotion composition contains a thermo-reversible gelling agent in an amount from about 1% by weight of the hydrophilic lotion composition to about 99.9% by weight of the hydrophilic lotion composition, more typically from about 2% by weight of the hydrophilic lotion composition to about 95% by weight of the hydrophilic lotion composition, and more typically from about 5% by weight of the hydrophilic lotion composition to about 90% by weight of the hydrophilic lotion composition.

In addition, a method of making the dry substrate formed of a first and second web is disclosed. Each of these webs may be formed with a single ply or multiple plies. First, a temperature change composition is applied on the first side of the first web and the first side of the second web and a hydrophilic lotion composition is applied on the second side of the first web and the second side of the second web. Then, the first web and second web are wound together to form a combined web so that the first side of the first web is facing the first side of the second web. Thus, the temperature change composition is between the first web and the second web of the dry substrate. The hydrophilic lotion composition is on the exterior surfaces of the dry substrate to maintain the temperature change composition within the tissue and to help prevent skin irritation during use.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Dry, as used herein to describe tissue or wiping products, means that the product is supplied without any moisture beyond the equilibrium moisture that is generally associated with the product. The "equilibrium moisture" is the moisture that the sheet contains when exposed to ambient conditions for extended periods of time. The equilibrium moisture within the sheet will not change with time at the same relative humidity and temperature. The dry products will have equilibrium moisture contents typically less than 15%, such as less than 10% such as from about 3% to about 8% under most ambient conditions that are encountered during routine use of the product.

The heat absorption factor, as used herein, expressed in $J/m^2$ is defined as the product of the heat of fusion of the cooling composition expressed in J/gram and the application rate of the cooling composition applied to the tissue product expressed in gsm.

Latent heat of fusion and melting points are determined by differential scanning calorimetry (DSC). Melting point, as defined herein, refers to the peak melt temperature as determined by DSC. Samples may be analyzed on a TA Instruments DSC 2920 Modulated DSC (Standard Cell) using the following experimental procedure: Approximately 5 mg of the respective material was weighed to the nearest 0.1 mg. Samples are run in the temperature interval from −50° C. to 100° C. with a heating/cooling rate of 10° C./min in an inert gas ($N_2$) atmosphere. The heat of fusion ($\Delta H_f$) is computed from the integral under the respective melting peak, with the reported results being the average value from 3 heating/cooling cycles.

The present disclosure is generally directed to dry wiping products, such as dry tissue products, that have improved perceived benefits. In particular, wiping products, when in contact with the skin, can provide a cooling sensation and feeling. The cooling sensation can, for instance, provide comfort and a soothing feeling to irritated skin. It is also found, that when used with a bath tissue, cooling can also evoke a sensation of wetness which can lead to a perception of improved cleaning. In one embodiment, the wiping product can be designed to provide a cooling sensation without substantial transfer of the phase change chemical composition to the skin of the user.

In one embodiment, for instance, a dry wiping product, such as a facial tissue product, that contains a temperature change composition is disclosed herein. The temperature change composition includes at least one phase change agent that undergoes a phase change when elevated in temperature. The phase change agent, for example, can have a relatively high heat of fusion which allows it to absorb great amounts of thermal energy and to regulate to a lower temperature than the environment. In particular, when the wiping product is heated such as being in contact with one's skin, the phase change agent quickly warms to its melting point. Due to the high heat of fusion, significant amounts of heat can then be absorbed while the phase change agent is melted. In turn, a cooling sensation is provided to the skin of the user.

Figure 1:
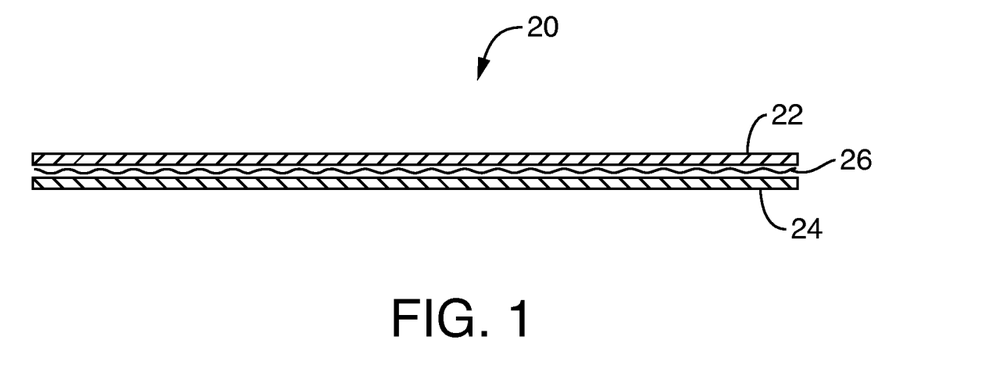
FIG. 1 is a cross-sectional view of the dry substrate illustrated in FIG. 1.

Referring to FIG. 1, one embodiment of a tissue product 10 made in accordance with the present disclosure is shown. The tissue product 10 can contain any suitable base sheet made from various different types of fiber furnishes. The tissue product 10 contains multiple tissue webs laminated or bonded or combined by any other means together.

Tissue webs that may be used to construct the tissue product 10, for instance, can generally contain pulp fibers either alone or in combination with other fibers. Each tissue web can generally have a bulk density of at least 2 cc/g, such as at least 3 cc/g.

Fibers suitable for making tissue webs contain any natural or synthetic cellulosic fibers including, but not limited to, nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898 issued Dec. 27, 1988 to Laamanen et al.; U.S. Pat. No. 4,594,130 issued Jun. 10, 1986 to Chang et al.; and U.S. Pat. No. 3,585,104 issued Jun. 15, 1971 to Kleinert. Useful fibers can also be produced by anthraquinone pulping, exemplified by U.S. Pat. No. 5,595,628 issued Jan. 21, 1997 to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Pulpex®, available from Hercules, Inc. (Wilmington, Del.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers may include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermo-mechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue web can also be utilized. For example, a papermaking process can utilize creping, wet creping, double creping, embossing, wet pressing, air pressing, through-air drying, creped through-air drying, uncreped through-air drying, hydroentangling, air laying, as well as other steps known in the art.

The tissue web may be formed from a fiber furnish containing pulp fibers in an amount of at least about 50% by weight, such as at least about 60% by weight, such as at least about 70% by weight, such as at least about 80% by weight, such as at least about 90% by weight, such as 100% by weight.

Also suitable for products are tissue sheets that are pattern densified or imprinted, such as the tissue sheets disclosed in any of the following U.S. Pat. No. 4,514,345 issued on Apr. 30, 1985 to Johnson et al.; U.S. Pat. No. 4,528,239 issued on Jul. 9, 1985 to Trokhan; U.S. Pat. No. 5,098,522 issued on Mar. 24, 1992 to Smurkoski et al.; U.S. Pat. No. 5,260,171 issued on Nov. 9, 1993 to Smurkoski et al.; U.S. Pat. No. 5,275,700 issued on Jan. 4, 1994 to Trokhan; U.S. Pat. No. 5,328,565 issued on Jul. 12, 1994 to Rasch et al.; U.S. Pat. No. 5,334,289 issued on Aug. 2, 1994 to Trokhan et al.; U.S. Pat. No. 5,431,786 issued on Jul. 11, 1995 to Rasch et al.; U.S. Pat. No. 5,496,624 issued on Mar. 5, 1996 to Steltjes, Jr. et al.; U.S. Pat. No. 5,500,277 issued on Mar. 19, 1996 to Trokhan et al.; U.S. Pat. No. 5,514,523 issued on May 7, 1996 to Trokhan et al.; U.S. Pat. No. 5,554,467 issued on Sep. 10, 1996 to Trokhan et al.; U.S. Pat. No. 5,566,724 issued on Oct. 22, 1996 to Trokhan et al.; U.S. Pat. No. 5,624,790 issued on Apr. 29, 1997 to Trokhan et al.; and U.S. Pat. No. 5,628,876 issued on May 13, 1997 to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The tissue web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents may include cationic debonding agents such as fatty dialkyl quaternary amine salts, mono fatty alkyl tertiary amine salts, primary amine salts, imidazoline quaternary salts, silicone quaternary salts and unsaturated fatty alkyl amine salts. Other suitable debonding agents are disclosed in U.S. Pat. No. 5,529,665 issued on Jun. 25, 1996 to Kaun which is incorporated herein by reference. In particular, Kaun '665 discloses the use of cationic silicone compositions as debonding agents.

In one embodiment, the debonding agent may be an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation (Greenwich, Conn.). The imidazoline-based debonding agent can be added in an amount of between 2 kg per metric tonne to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

Optional chemical additives may also be added to the aqueous papermaking furnish or to the formed embryonic web to impart additional benefits to the product and process and are not antagonistic to the intended benefits of the dry substrate. The following materials are included as examples of additional chemicals that may be applied to the web along with the temperature change composition or hydrophilic lotion composition. The chemicals are included as examples and are not intended to limit the scope of the invention. Such chemicals may be added at any point in the papermaking process, including being added simultaneously with the additive composition in the pulp making process, wherein said additive or additives are blended directly with the additive composition.

Additional types of chemicals that may be added to the paper web include, but are not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general, and the like, may also be incorporated into the finished products.

In general, the products of the present invention can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Tissue webs that may be treated with the temperature change composition and hydrophilic lotion composition may include a single homogenous layer or ply of fibers or may include a stratified or layered construction. For instance, the tissue web ply may include two or three layers or plies of fibers. Each layer may have a different fiber composition.

Each of the fiber layers contains a dilute aqueous suspension of papermaking fibers. The particular fibers contained in each layer generally depend upon the product being formed and the desired results. In one embodiment, for instance, a middle layer contains southern softwood kraft fibers either alone or in combination with other fibers, such as high yield fibers. The outer layers, on the other hand, can contain softwood fibers, such as northern softwood kraft.

In an alternative embodiment, the middle layer may contain softwood fibers for strength, while the outer layers may contain hardwood fibers, such as eucalyptus fibers, for a perceived softness.

The basis weight of tissue webs can vary depending upon the final product. For example, the process may be used to produce facial tissues, bath tissues, paper towels, industrial wipers, and the like. In general, the basis weight of the tissue products may vary from about 10 gsm to about 80 gsm, such as from about 20 gsm to about 60 gsm. For bath and facial tissues, for instance, the basis weight may range from about 10 gsm to about 60 gsm. For paper towels, on the other hand, the basis weight may range from about 25 gsm to about 80 gsm.

The tissue web bulk may also vary from about 2 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc. (Newberg, Oreg.). The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will generally be the same as indicated above, such as from about 20 gsm to about 80 gsm. Thus, the basis weight of each ply can be from about 5 gsm to about 60 gsm, such as from about 10 gsm to about 40 gsm.

In accordance with the present disclosure, the tissue product 10 contains a temperature change composition for imparting a cooling sensation to the skin of a user. The operative temperature change composition contains an effective amount of at least one phase change agent. The temperature change composition may be incorporated into the tissue product in a manner so that substantially none of the temperature change composition is present on the exterior surfaces. For instance, referring to FIG. 1, a tissue product 10 is shown that is comprised of a first tissue web 22 laminated or bonded or combined by any other means to a second tissue web 24. As shown, positioned in between the first tissue web 22 and the second tissue web 24 is a temperature change composition 26. By locating the temperature change composition 26 in between the tissue webs, the temperature change composition is substantially minimized from coming in contact or being transferred to a user's skin. When the tissue product 20, however, is held against the skin, body heat will be absorbed by the temperature change composition 26 through the tissue webs thus elevating in temperature. The increase in temperature will cause a phase change to occur in the phase change agent providing a cooling sensation to the skin of the user.

The temperature change composition includes at least one phase change agent that undergoes a phase change when heated which, in turn, provides a cooling sensation to the skin. The temperature change composition can be incorporated into the tissue product 10 using any suitable method or technique. For example, the temperature change composition can be sprayed onto the tissue product, extruded onto the tissue product, or printed onto the tissue product using, for instance, flexographic printing, direct gravure printing, or indirect gravure printing. In still another embodiment, the temperature change composition can be applied to the tissue product using any suitable coating equipment, such as a knife coater or slot coater. As the temperature change composition is solid at room temperature in one embodiment, it may be desirable to melt the composition prior to application to the tissue web. The application of such molten materials to a finished tissue web is well known in the art. At times it may also be advantageous to cool the web directly after application of the molten phase change agent, especially when the treated product is wound into a spirally wound roll either for a finished product or for further processing. The cooling of the web below the melting point of the phase change agent reduces the potential of the spirally wound web from becoming "blocked". "Blocked" as used herein refers to the tendency of adjacent facing sheets in the spirally wound roll to adhere to each other and restrict the ability to unwind the web from the spirally wound roll.

In general, a phase change agent includes any substance that has the capability of absorbing or releasing thermal energy to reduce or eliminate heat flow at or within a temperature stabilizing range. The temperature stabilizing range may include a particular transition temperature or range of transition temperatures. A phase change agent preferably will be capable of altering a flow of thermal energy during a time when the phase change agent is absorbing or releasing heat, typically as the phase change agent undergoes a transition between two states (e.g., liquid and solid states, liquid and gaseous states, solid and gaseous states, or two solid states). This action is typically transient, meaning it will occur until a latent heat of the phase change agent is absorbed or released during a heating or cooling process. Thermal energy may be stored or removed from the phase change agent, and the phase change agent typically can be effectively recharged by a source of heat or cold. The temperature change compositions may exhibit a phase change at temperatures between about 23° C. and about 35° C. such as to be appropriate for use in cooling skin. Materials may also be chosen with transition temperatures between about 23° C. and about 32° C., between about 26° C. and about 32° C., or within any other suitable range. The phase change temperature is selected such that the phase change occurs between the ambient temperature of the product and the external temperature of the user's skin.

The temperature change composition may contain a mixture of phase change agents that have a mixture of transition temperatures. When a mixture of phase change agents is used, the components can be selected so as to have a collective melting point within the above mentioned limits. In some cases the melting points of the individual phase change agents comprising the temperature change composition may lie outside the melting point limits for the phase change temperature of the temperature change composition. However, the mixture of phase change agents will display a phase change within the desired temperature limits. When the temperature change composition is held against the skin either directly or indirectly, the composition warms to the temperature of the skin from room temperature. The phase change agent then melts at its specified phase change temperature. That melting requires heat, which is taken from the skin, imparting a feeling of cooling. Once the material is melted, the cooling sensation dissipates. Having a range of phase change temperatures (melting points in this case) of the phase change agents may extend the range of temperatures where cooling is felt. In one example, a combination of phase change agents having phase change temperatures at 18° C., 28° C., and 35° C. are combined to create a temperature change composition having a melting point between 23° C. and 32° C.

Suitable phase change agents include, by way of example and not by limitation, encapsulated phase change powder, (e.g., LURAPRET, a purified, encapsulated paraffin available from BASF and MPCM 43-D available from Microtek Laboratories), hydrocarbons (e.g., straight chain alkanes or paraffinic hydrocarbons, branched-chain alkanes, unsaturated hydrocarbons, halogenated hydrocarbons, and alicyclic hydrocarbons), waxes, natural butters, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol,2-hydroxymethyl-2-methyl-1,3-propanediol, pentaerythritol, dipentaerythritol, pentaglycerine, tetramethylol ethane, neopentyl glycol, tetramethylol propane, monoaminopentaerythritol, diaminopentaerythritol, and tris(hydroxymethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers comprising polyethylene, polyethylene glycol, polypropylene, polypropylene glycol, or polytetramethylene glycol), and mixtures thereof. Desirable examples of phase change materials include tricaprin, parrafin, nonadecane, octadecane, stearyl heptanoate, lauryl lactate, lauryl alcohol, capric acid, caprylic acid, cetyl babassuate, mangifera indica (mango) seed butter, theobroma cacao (cocoa) seed butter, butyrospermum parkii butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

As described above, in one embodiment, the temperature change composition may contain a mixture of two or more phase change agents. In one particular embodiment, the temperature change composition contains a mixture of stearyl heptanoate and n-octadecane.

Phase change agents may include phase change agents in a non-encapsulated form and phase change agents in an encapsulated form. A phase change agent in a non-encapsulated form may be provided as a solid in a variety of forms (e.g., bulk form, powders, pellets, granules, flakes, paste and so forth) or as a liquid in a variety of forms (e.g., molten form, dissolved in a solvent, and so forth).

Another aspect of the temperature change compositions is the heat of fusion of the temperature change composition comprising the phase change agents. The temperature change compositions can have heats of fusion of at least about 100 J/g. For instance, in one embodiment, the temperature change composition contains a hydrocarbon as the phase change agent, such as a straight chain hydrocarbon. The hydrocarbon, for instance, may contain more than about 12 carbon atoms in the chain, such as from about 18 carbon atoms to about 19 carbon atoms in the chain. Particular examples of phase change agents include, for instance, octadecane (heat of fusion of about 213.0 J/g), nonadecane, stearyl heptanoate, and mixtures thereof.

Perhaps more importantly, however, is the heat absorption factor of the products. The heat absorption factor, expressed in $J/m^2$, is the product of the heat of fusion of the temperature change composition expressed in J/gram and the application rate of the temperature change composition applied to the tissue product expressed in gsm. The heat absorption factor of the products can be at least about 500 J/m$^2$, such as at least about 1000 J/m$^2$ such as from about 1000 J/m$^2$ to about 4000 J/m$^2$ or greater. For many applications, the temperature change composition can be applied to a tissue web such that the phase change agents are present on the web in an amount from about 4 gsm to about 40 gsm.

In one specific embodiment the cooling tissue product is a facial tissue comprising three or more plies, two outer plies and one or more interior plies. The temperature change composition is applied to at least one of the one or more interior plies. In another embodiment, the cooling tissue product is a facial tissue comprising two plies, comprising two outer facing surfaces and two opposing facing inner surfaces. The phase change composition is applied to one or both of the opposing facing inner surfaces. In another embodiment, the product is a multi-ply tissue product where the phase change composition is applied selectively to the inner portion of the multi-ply product so as to minimize blocking.

A hydrophilic lotion composition 28 is applied to the exterior surface of the tissue product and used in conjunction with the temperature change composition 26. "Hydrophilic" as used herein means water miscible. The hydrophilic lotion composition creates a hydrophilic surface and restores absorbency to the treated sheet while creating a high energy surface that is not wettable by the melted phase change material. In this manner, the tissue product 20 can not only provide a cooling sensation to the user, but can also prevent transfer of the phase change agent onto the skin by holding the phase change agents within the substrate. With prior temperature change compositions, disclosed in for example, PCT Patent Application No. PCT/IB2009/051515 entitled "Tissue Products having a Cooling Sensation When Contacted with Skin," the phase change materials transfer to the skin and cause irritation.

The hydrophilic lotion composition contains a carrier and a thermo-reversible gelling agent, the lotion being located on at least an exterior surface of the substrate and preferably on both exterior surfaces of the substrate.

Carriers for use in the hydrophilic lotion composition may include, but are not limited to, water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof. Desirably, the carrier is propylene glycol.

Typically, the hydrophilic lotion composition contains a carrier in an amount from about 1% by weight of the hydrophilic lotion composition to about 99.9% by weight of the hydrophilic lotion composition, more typically from about 2% by weight of the hydrophilic lotion composition to about 95% by weight of the hydrophilic lotion composition, and more typically from about 5% by weight of the hydrophilic lotion composition to about 90% by weight of the hydrophilic lotion composition.

Thermo-reversible gelling agents are defined as ingredients that are soluble, partially soluble, or miscible in a hydrophilic carrier at elevated temperatures, such as 50° C., that have the ability to thicken the carrier when cooled to 25° C., but will be less viscous at 50° C. when application to a substrate is necessary. Suitable hydrophilic carriers include water, glycols and, in particular, propylene glycol. Thermo-reversible gelling agents for use in the hydrophilic lotion composition may include, but are not limited to, salts of fatty acids such as sodium stearate, sodium palmitate, potassium stearate. These salts can be added to the composition or can be created in-situ by addition of the fatty acid and neutralizing with appropriate base. An example of in-situ formation of the hydrophilic lotion composition is to provide stearic acid and sodium hydroxide to produce sodium stearate.

Other desirable thermo-reversible gelling agents could include, but are not limited to, polyethylene glycols and derivatives such as PEG-20, PEG-150 distearate, PEG-150 pentaerythrityl tetrastearate, disteareth-75 IPDI, disteareth-100 IPDI, fatty alcohols such as cetyl alcohol, fatty acids such as stearic acid, hydroxystearic acid and its derivatives, and combinations thereof.

Typically, the hydrophilic lotion composition contains a thermo-reversible gelling agent in an amount from about 1% by weight of the hydrophilic lotion composition to about 99.9% by weight of the hydrophilic lotion composition, more typically from about 2% by weight of the hydrophilic lotion composition to about 95% by weight of the hydrophilic lotion composition, and more typically from about 5% by weight of the hydrophilic lotion composition to about 90% by weight of the hydrophilic lotion composition.

In addition to the carrier and thermo-reversible gelling agent, the hydrophilic lotion composition can contain various other ingredients and components. Examples of other ingredients that may be included within the hydrophilic lotion composition are emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Thus, the hydrophilic lotion compositions may further optionally include one or more emollients, which typically act to soften, soothe, and otherwise lubricate and/or moisturize the skin. Suitable emollients that can be incorporated into the compositions include oils such as natural oils such as jojoba, sunflower, safflower, and the like, synthetic based oils such as petrolatum, mineral oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, glycerol esters and derivatives, propylene glycol esters and derivatives, fatty acid esters and derivatives, alkoxylated carboxylic acids, alkoxylated alcohols, and combinations thereof.

Ethers such as eucalyptol, cetearyl glucoside, dimethyl isosorbic polyglyceryl-3 cetyl ether, polyglyceryl-3 decyltetradecanol, propylene glycol myristyl ether, and combinations thereof, can also suitably be used as emollients.

The hydrophilic lotion composition may include one or more emollients in an amount from about 0.01% by weight of the hydrophilic lotion composition to about 70% by weight of the hydrophilic lotion composition, more desirably from about 0.05% by weight of the hydrophilic lotion composition to about 50% by weight of the hydrophilic lotion composition, and even more desirably from about 0.1% by weight of the hydrophilic lotion composition to about 40% by weight of the hydrophilic lotion composition.

The hydrophilic lotion composition may include one or more viscosity enhancers in an amount from about 0.01% by weight of the hydrophilic lotion composition to about 25% by weight of the hydrophilic lotion composition, more desirably from about 0.05% by weight of the hydrophilic lotion composition to about 10% by weight of the hydrophilic lotion composition), and even more desirably from about 0.1% by weight of the hydrophilic lotion composition to about 5% by weight of the hydrophilic lotion composition.

The hydrophilic lotion composition may optionally further contain humectants. Examples of suitable humectants include glycerin, glycerin derivatives, sodium hyaluronate, betaine, amino acids, glycosaminoglycans, honey, sorbitol, glycols, polyols, sugars, sugar alcohols, hydrogenated starch hydrolysates, salts of PCA, lactic acid, lactates, and urea. A particularly preferred humectant is glycerin. The hydrophilic lotion composition may suitably include one or more humectants in an amount from about 0.05% by weight of the hydrophilic lotion composition to about 25% by weight of the hydrophilic lotion composition.

The hydrophilic lotion composition may optionally further contain film formers. Examples of suitable film formers include lanolin derivatives (e.g., acetylated lanolins), superfatted oils, cyclomethicone, cyclopentasiloxane, dimethicone, synthetic and biological polymers, proteins, quaternary ammonium materials, starches, gums, cellulosics, polysaccharides, albumen, acrylates derivatives, IPDI derivatives, and the like. The composition of the present disclosure may suitably include one or more film formers in an amount from about 0.01% by weight of the hydrophilic lotion composition to about 20% by weight of the hydrophilic lotion composition.

The hydrophilic lotion composition may optionally further contain slip modifiers. Examples of suitable slip modifiers include bismuth oxychloride, iron oxide, mica, surface treated mica, ZnO, ZrO$_2$, silica, silica silyate, colloidal silica, attapulgite, sepiolite, starches (i.e. corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like. The hydrophilic lotion composition may suitably include one or more slip modifiers in an amount from about 0.01% by weight of the hydrophilic lotion composition to about 20% by weight of the hydrophilic lotion composition.

The hydrophilic lotion composition may also further contain surface modifiers. Examples of suitable surface modifiers include silicones, quaternium materials, powders, salts, peptides, polymers, clays, and glyceryl esters. The hydrophilic lotion composition may suitably include one or more surface modifiers in an amount from about 0.01% by weight of the hydrophilic lotion composition to about 20% by weight of the hydrophilic lotion composition.

The hydrophilic lotion composition may also further contain skin protectants. Examples of suitable skin protectants include ingredients referenced in SP Monograph (21 CFR part 347). Suitable skin protectants and amounts include those set forth in SP Monograph, Subpart B—Active Ingredients Sec 347.10: (a) Allantoin, 0.5 to 2%, (b) Aluminum hydroxide gel, 0.15 to 5%, (c) Calamine, 1 to 25%, (d) Cocoa butter, 50 to 100%, (e) Cod liver oil, 5 to 13.56%, in accordance with 347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1 to 30%, (h) Glycerin, 20 to 45%, (i) Hard fat, 50 to 100%, (j) Kaolin, 4 to 20%, (k) Lanolin, 12.5 to 50%, (l) Mineral oil, 50 to 100%; 30 to 35% in combination with colloidal oatmeal in accordance with §347.20(a)(4), (m) Petrolatum, 30 to 100%, (n) Sodium bicarbonate, (o) Topical starch, 10 to 98%, (p) White petrolatum, 30 to 100%, (q) Zinc acetate, 0.1 to 2%, (r) Zinc carbonate, 0.2 to 2%, (s) Zinc oxide, 1 to 25%.

The hydrophilic lotion composition may also further contain quaternary ammonium materials. Examples of suitable quaternary ammonium materials include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like. The hydrophilic lotion composition may suitably include one or more quaternary materials in an amount from about 0.01% by weight of the hydrophilic lotion composition to about 20% by weight of the hydrophilic lotion composition.

The hydrophilic lotion composition may optionally further contain surfactants. Examples of suitable additional surfactants include, for example, anionic surfactants, cationic surfactants, amphoteric surfactants, zwitterionic surfactants, non-ionic surfactants, and combinations thereof. Specific examples of suitable surfactants are known in the art and include those suitable for incorporation into hydrophilic lotion compositions and wipes. The hydrophilic lotion composition may suitably include one or more surfactants in an amount from about 0.01% by weight of the hydrophilic lotion composition to about 20% by weight of the hydrophilic lotion composition.

The hydrophilic lotion composition may also further contain additional emulsifiers. As mentioned above, the natural fatty acids, esters and alcohols and their derivatives, and combinations thereof, may act as emulsifiers in the composition. Optionally, the composition may contain an additional emulsifier other than the natural fatty acids, esters and alcohols and their derivatives, and combinations thereof. Examples of suitable emulsifiers include nonionics such as polysorbate 20, polysorbate 80, anionics such as DEA phosphate, cationics such as behentrimonium methosulfate, and the like. The hydrophilic lotion composition may suitably include one or more additional emulsifiers in an amount from about 0.01% by weight of the hydrophilic lotion composition to about 20% by weight of the hydrophilic lotion composition.

The hydrophilic lotion composition may additionally include adjunct components conventionally found in pharmaceutical compositions in their art-established fashion and at their art-established levels. For example, the compositions may contain additional compatible pharmaceutically active materials for combination therapy, such as antimicrobials, antioxidants, anti-parasitic agents, antipruritics, antifungals, antiseptic actives, biological actives, astringents, keratolytic actives, local anesthetics, anti-stinging agents, anti-reddening agents, skin soothing agents, and combinations thereof. Other suitable additives that may be included in the hydrophilic lotion compositions include colorants, deodorants, fragrances, perfumes, emulsifiers, anti-foaming or defoaming agents, lubricants, natural moisturizing agents, skin conditioning agents, skin protectants and other skin benefit agents (e.g., extracts such as aloe vera and anti-aging agents such as peptides), solvents, solubilizing agents, suspending agents, wetting agents, humectants, preservatives, pH adjusters, buffering agents, dyes and/or pigments, and combinations thereof.

Figure 2:
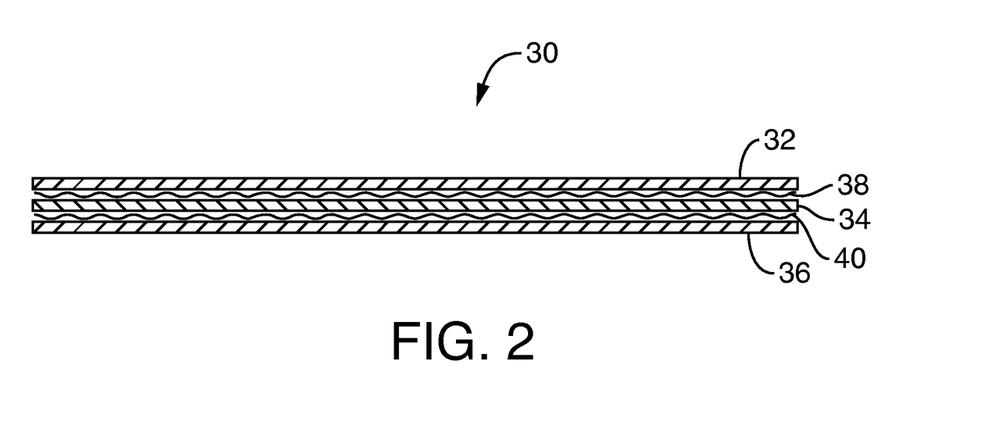
FIG. 2 is a cross-sectional view of another embodiment of a dry substrate made in accordance with the present disclosure.
Figure 3:
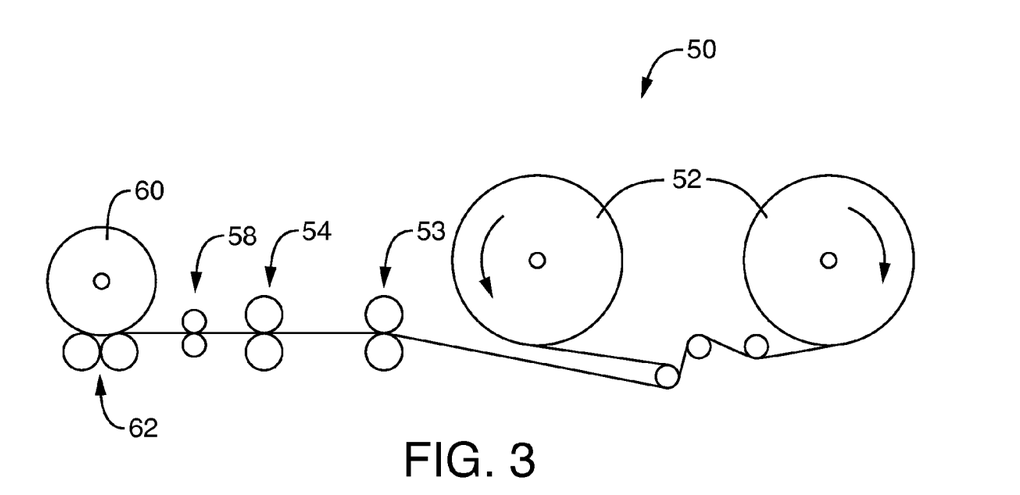
FIG. 3 is a schematic illustration of an exemplary converting operation for the dry substrate made in accordance with the present disclosure.

In addition to a product having two webs as shown in FIG. 2, other tissue products that may be made in accordance with the present disclosure can include more than two webs. For example, a 3-web tissue product 30 is illustrated in FIG. 3. As shown, the tissue product 30 includes a middle tissue web 34 laminated or bonded or combined by other any means to outer tissue webs 32 and 36. A temperature change composition is located in between the first tissue web 32 and the middle tissue web 34. A temperature change composition 40 is also positioned in between the middle tissue web 34 and the second outer tissue web 36.

Furthermore, each or the tissue webs may be a single ply or multiple plies. In one desirable embodiment, each of tissue webs contains two plies.

Referring now to FIG. 3, a converting line 50 is schematically illustrated. Two rolls 52 of tissue web are provided. The tissue webs have a first side 64 and a second side 66.

Figure 4:
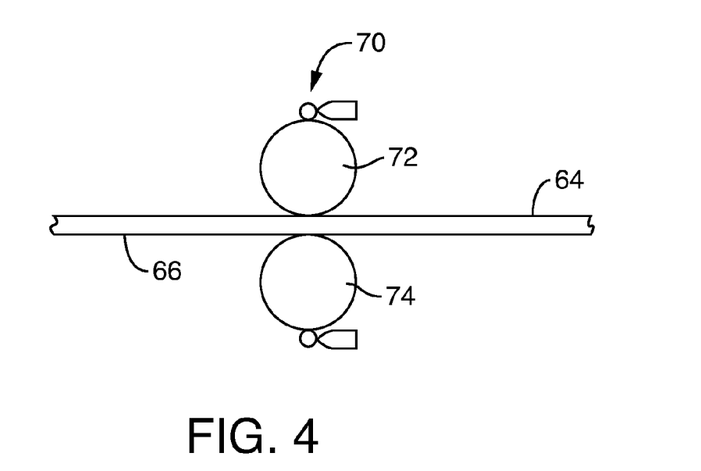
FIG. 4 is a schematic illustration of an exemplary printing operation for the dry substrate made in accordance with the present disclosure.

Prior to converting, each of the tissue's webs passes through a gravure coater 70 as illustrated in FIG. 4. Each gravure coater 70 has two gravure rolls 72, 74. The first gravure roll 72 contains the temperature change composition including the phase change material, while the second gravure roll 74 contains the hydrophilic lotion composition. The first gravure roll 72 applies the temperature change composition to a first side 64 of both rolls of the tissue web. The second gravure roll 74 applies the hydrophilic lotion composition to a second side 66 of both rolls of the tissue web.

The rewinding machine plies together the two rolls 52 of tissue web into a combined web. The two rolls of tissue 52 are wound together such that the first side 64 of the first web and the first side 64 of the second web are facing each other. Thus, the temperature change composition is between the first web and the second web, and the hydrophilic lotion composition is present on the exterior surfaces of the combined web.

If a web is provided with the temperature change composition on both sides of the web, blocking may occur during the production process. By providing two webs with the temperature change composition on a first side, and a hydrophilic lotion composition on a second side, blocking issues can be reduced. Thus, the described method is a more efficient process to produce the tissue product.

The combined web then can optionally pass through a calender 52 or multiple calenders. The calender can utilize metallic non-compressive rolls; compressive rolls such as urethane, paper, rubber, or composite; or use a combination of a non-compressive roll with a compressive roll. The calendar can be operated in a nipped condition to a fixed load, or in a gap mode to a fixed gap, or in a gap mode with one of the rolls traveling at a rate faster than the web's speed.

After calendering, the combined web then can optionally pass through a crimping station 54. The crimping station includes an anvil roll and a plurality of crimping wheels. The crimping wheels emboss the combined web such that the two webs become attached to one another.

The combined web then passes through a slitter 58 and is wound into a hardroll 60 by a winder 62. Subsequent converting equipment, known to those of skill in the art, can unwind the two-ply hardroll, cut, fold, and package the hardroll to form a box of facial tissues.

EXAMPLES

The present disclosure may be better understood with reference to the following examples.

Comparative Example 1

Comparative Example 1 represents a commercial, lotion treated facial tissue for a control product. A three-ply creped tissue sheet having a finished basis weight of 44 gsm consisting of 70 percent hardwood and 30 percent softwood fibers was used. Each ply was made from a stratified fiber furnish including two outer layers and a middle layer. A hydrophobic lotion treatment composition was heated to a temperature of 63° C. and printed on both outer sides of the three-ply tissue product via a simultaneous offset rotogravure printing process. The fluid reservoirs of the printer were heated to 63° C. to insure the hydrophobic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The three-ply facial tissue is treated with the hydrophobic lotion treatment composition for a final treatment level of 7.8 gsm. The composition of the hydrophobic lotion treatment is shown below in Table 1.

TABLE 1

| Hydrophobic Lotion Treatment Composition | |
|---|---|
| Ingredient | Wt. % |
| Mineral oil | 60% |
| Isopropyl Palmitate | 3% |
| Dimethicone | 1% |
| Ceresin Wax | 18% |
| Stearyl Alcohol | 18% |

Comparative Example 2

Comparative Example 2 represents a hydrophilic lotion treated facial tissue with no phase change material. A three-ply creped tissue sheet having a finished basis weight of 44 gsm consisting of 70 percent hardwood and 30 percent softwood fibers was used. Each ply was made from a stratified fiber furnish including two outer layers and a middle layer. A hydrophilic lotion treatment composition was heated to a temperature of 63° C. and printed on both outer sides of the three-ply tissue product via a simultaneous offset rotogravure printing process. The fluid reservoirs of the printer were heated to 63° C. to insure the hydrophillic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The three-ply facial tissue is treated with the hydrophilic lotion treatment composition with a single pass for a final treatment level of 12.5 gsm. The composition of the hydrophilic lotion treatment composition 1 is shown below in Table 2.

TABLE 2

Hydrophilic Lotion Treatment Composition 1

| Ingredient | Wt. % |
|---|---|
| Propylene glycol | 95% |
| Sodium Stearate | 5% |

Comparative Example 3

Comparative Example 3 represents a facial tissue with an inner phase change material but no outer treatment layer. A two-ply creped tissue sheet having a finished basis weight of 30 gsm consisting of 70 percent hardwood and 30 percent softwood fibers was used. Each ply was made from a stratified fiber furnish including two outer layers and a middle layer. A temperature change composition of n-octadecane (commercially available from Chevron-Philips) was heated to a temperature of 40° C. and printed on both outer sides of the two-ply tissue product via a simultaneous offset rotogravure printing process. The fluid reservoirs of the printer were heated to 40° C. to insure the phase change material remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue was treated with melted n-octadecane and printed onto both sides of the two-ply tissue substrate. The tissue substrate was treated two times for a final treatment level of 11.1 gsm. In addition, a two-ply untreated tissue web was prepared for an outer-layer.

The rolls were positioned on two unwinds such that the phase change material treated roll was situated in front of the roll for the outer layer. The plies on the roll for the outer layers were separated to sandwich the two-ply sheet from the roll treated with the phase change material. The resulting four-ply structure was calendared, crimped, and slit to standard facial tissue width. The four-ply finished product was composed of two inner plies treated with a phase change material and two outer plies with no treatment. The outer plies with no treatment would come in direct contact with skin during use.

Comparative Example 4

Comparative Example 4 represents a facial tissue with an inner phase change material with a hydrophobic lotion treatment layer. A two-ply creped tissue sheet having a finished basis weight of 30 gsm consisting of 70 percent hardwood and 30 percent softwood fibers was used. Each ply was made from a stratified fiber furnish including two outer layers and a middle layer. A temperature change composition of stearyl heptanoate (Tegasoft SH commercially available from Evonik, Inc.) was heated to a temperature of 40° C. and printed on both outer sides of the two-ply tissue product via a simultaneous offset rotogravure printing process. The fluid reservoirs of the printer were heated to 40° C. to insure the phase change material remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue was treated with melted stearyl heptanoate and printed onto both sides of the two-ply tissue substrate. The tissue substrate was treated two passes for a final treatment level of 13.7 gsm.

In addition, a two-ply creped tissue sheet having a finished basis weight of 30 gsm consisting of 70 percent hardwood and 30 percent softwood fibers was used. Each ply was made from a stratified fiber furnish including two outer layers and a middle layer. A hydrophobic lotion treatment composition was heated to a temperature of 63° C. and printed on both outer sides of the two-ply tissue product via a simultaneous offset rotogravure printing process. The fluid reservoirs of the printer were heated to 63° C. to insure the hydrophobic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue is treated with the hydrophobic lotion treatment composition of Comparative Example 1 for a final treatment level of 7.8 gsm.

The two rolls were then positioned on two unwinds such that the phase change material treated roll was situated in front of the roll for the outer layer having the hydrophobic lotion composition. The plies on the roll for the outer layers were separated to sandwich the two-ply sheet from the roll treated with the phase change material. The resulting four-ply structure was calendared, crimped, and slit to standard facial tissue width. The four-ply finished product was composed of two inner plies treated with a phase change material and two outer plies with a hydrophobic lotion treatment. The outer plies with the hydrophobic lotion treatment would come in direct contact with skin during use.

Comparative Example 5

Comparative Example 5 represents another facial tissue with an inner phase change material with a hydrophobic lotion treatment layer. A two-ply creped tissue sheet having a finished basis weight of 30 gsm consisting of 70 percent hardwood and 30 percent softwood fibers was used. Each ply was made from a stratified fiber furnish including two outer layers and a middle layer. A temperature change composition of n-octadecane (commercially available from Chevron-Philips) was heated to a temperature of 40° C. and printed on both outer sides of the two-ply tissue product via a simultaneous offset rotogravure printing process. The fluid reservoirs of the printer were heated to 40° C. to insure the phase change material remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue was treated with melted n-octadecane and printed onto both sides of the two-ply tissue substrate. The tissue substrate was treated two times for a final treatment level of 11.1 gsm.

In addition, a two-ply creped tissue sheet having a finished basis weight of 30 gsm consisting of 70 percent hardwood and 30 percent softwood fibers was used. Each ply was made from a stratified fiber furnish including two outer layers and a middle layer. A hydrophobic lotion treatment composition was heated to a temperature of 63° C. and printed on both outer sides of the two-ply tissue product via a simultaneous offset rotogravure printing process. The fluid reservoirs of the printer were heated to 63° C. to insure the hydrophobic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.375 inch interference between the gravure rolls and the rubber backing rolls and 0.003 inch clearance between the facing rubber backing rolls. The simultaneous offset/offset gravure printer was run at 150 feet/minute. The two-ply facial tissue is treated with the hydrophobic lotion treatment composition of Comparative Example 1 for a final treatment level of 7.8 gsm.

The two rolls were then positioned on two unwinds such that the phase change material treated roll was situated in front of the roll for the outer layer having the hydrophobic lotion composition. The plies on the roll for the outer layers were separated to sandwich the two-ply sheet from the roll treated with the phase change material. The resulting four-ply structure was calendared, crimped, and slit to standard facial tissue width. The four-ply finished product was composed of two inner plies treated with a phase change material and two outer plies with a hydrophobic lotion treatment. The outer plies with the hydrophobic lotion treatment would come in direct contact with skin during use.

Example 1

Example 1 represents a facial tissue with an inner phase change material layer and an outer hydrophilic lotion treatment layer. A two-ply creped tissue sheet having a finished basis weight of 30 gsm consisting of 70 percent hardwood and 30 percent softwood fibers was used. Each ply was made from a stratified fiber furnish including two outer layers and a middle layer. A phase change material of n-octadecane (commercially available from Chevron-Philips) was heated to a temperature of 40° C. and printed on both outer sides of the two-ply tissue product via a simultaneous offset rotogravure printing process. The fluid reservoirs of the printer were heated to 40° C. to insure the phase change material remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue was treated with melted n-octadecane and printed onto both sides of the two-ply tissue substrate. The tissue substrate was treated two times for a final treatment level of 11.1 gsm.

In addition, a two-ply creped tissue sheet having a finished basis weight of 30 gsm consisting of 70 percent hardwood and 30 percent softwood fibers was used. Each ply was made from a stratified fiber furnish including two outer layers and a middle layer. A hydrophilic lotion treatment composition was heated to a temperature of 63° C. and printed on both outer sides of the two-ply tissue product via a simultaneous offset rotogravure printing process. The fluid reservoirs of the printer were heated to 63° C. to insure the hydrophilic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute. The two-ply facial tissue is treated with the hydrophilic treatment composition of Comparative Example 2 for a final treatment level of 11.8 gsm.

The rolls were positioned on two unwinds such that the phase change material treated roll was situated in front of the roll for the outer layer having the hydrophilic lotion composition. The plies on the roll for the outer layers were separated to sandwich the two-ply sheet from the roll treated with the phase change material. The resulting four-ply structure was calendared, crimped, and slit to standard facial tissue width. The four-ply finished product was composed of two inner plies treated with a phase change material and two outer plies with a hydrophilic lotion treatment. The outer plies with the hydrophilic lotion treatment would come in direct contact with skin during use.

Experiment 1

Comparative Examples 1-5 and Example 1 were evaluated in clinical and sensory tests. A Nose Irritation Study evaluated the skin alongside the nasal region after frequent repeated wiping with the tissue substrate. The Adaptable Methodology Panel (AMP) evaluated tissue characteristics, including those associated with cooling and residue (as measured by auditory intensity). Results from these studies are illustrated in Table 3 and summarized below. For the characteristics, examples with the same letter are similar in that attribute, and examples with letter A are considered to have the most of that characteristic. Treatment levels are the total treatment applied to the 2 sides of the treated tissue.

TABLE 3

Clinical/Sensory Study Results

| Code | # of Plies | Outer Treatment | PCM Inner Treatment | Cooling Perception | Auditory Intensity | Skin Damage | Redness |
|---|---|---|---|---|---|---|---|
| Comp. Ex. 1 | 3 | Hydrophobic (7.8 gsm) | None | D | BC | C | C |
| Comp. Ex. 2 | 3 | Hydrophilic (12.5 gsm) | None | CD | B | C | C |
| Comp. Ex. 3 | 4 | None | n-octadecane (11.1 gsm) | AB | A | A | A |
| Comp. Ex. 4 | 4 | Hydrophobic (7.8 gsm) | Tegosoft SH (13.7 gsm) | B | C | B | B |
| Comp. Ex. 5 | 4 | Hydrophobic (7.8 gsm) | n-octadecane (11.1 gsm) | C | CD | B | B |
| Example 1 | 4 | Hydrophilic (11.8 gsm) | n-octadecane (11.1 gsm) | A | B | C | C |

Comparative Example 1 serves as the performance benchmark for the cooling tissue in terms of auditory intensity and low skin damage and redness. Comparative Example 1 control product is not perceived to be cooling.

Comparative Example 2 is also not perceived to be cooling. Comparative Example 2 is comparable in terms of auditory intensity, skin damage, and redness to Comparative Example 1.

Comparative Example 3 provides a cooling sensation but has high residue, or higher auditory intensity, and causes irritation to the skin. The phase change material in Comparative Example 3 has likely wicked to the tissue surface and become available for direct contact with the skin without use of a hydrophilic lotion composition.

Comparative Example 4 is cooling, has acceptable auditory intensity, but is more damaging to the skin then Comparative Example 1 and 2. Since the outer lotion is hydrophobic, some of the phase change material may have migrated to the tissue surface or wicked to the surface on melting and become available for direct contact with the skin.

Comparative Example 5 tissue has acceptable residue (auditory intensity), but is only slightly cooling and is more damaging to the skin than Comparative Examples 1 and 2. The hydrophobic outer layer treatment has reduced the residue, skin damage, and redness when compared to Comparative Example 3, but reduces the cooling sensation. It appears that components from the hydrophobic treatment may have mixed with the n-octadecane to disrupt its crystallinity and cooling. It is also likely that some of the n-octadecane has migrated or wicked to the tissue surface on melting and has become available for direct contact with the skin.

Example 1 has excellent cooling characteristics and compares favorably with acceptable residue (auditory intensity), skin damage, and redness when compared to Comparative Examples 1 and 2. In addition, Example 1 is more cooling than Comparative Examples 4 and 5, but does not have the deficiencies of skin damage and redness. Finally, Example 1 is as cooling as Comparative Example 3, without having the deficiencies of residue (auditory intensity), skin damage, and redness. Use of an outer hydrophilic lotion treatment with the phase change material provides a combination of the best attributes.

Experiment 2

Stacks comprised of 50-90 treated tissues from Comparative Examples 2-5 and Example 1 were placed in cartons and evaluated in a one month aging study. Stack size varied by the number of plies in each sheet. Cartons containing four-ply sheets typically had 50-60 count stacks whereas cartons containing three-ply sheets typically had 90 count stacks. All cartons were filled such that the top sheet was in contact with the top, inner surface of the carton. The cartons were inspected after storage for one month at both 25° C. and 55° C. Packaging observations are indicated as mild with grease-like buildup and/or staining on bottom of carton; moderate with grease-like buildup and/or staining on bottom and sides of carton; and severe with grease-like buildup and/or staining on bottom, sides, and top of carton. The results are shown below in table 4.

TABLE 4

Packaging Aging Study Results

| Code | # of Plies | Outer Treatment | PCM Inner Treatment | Ambient Temperature (1 month @ 25° C.) Packaging Observation | Elevated Temperature (1 month @ 55° C.) Packaging Observation |
|---|---|---|---|---|---|
| Comp. Ex. 4 | 4 | Hydrophobic (7.8 gsm) | Stearyl heptanoate (13.7 gsm) | Moderate | Moderate |
| Comp. Ex. 5 | 4 | Hydrophobic (7.8 gsm) | n-Octadecane (11.1 gsm) | Moderate | Moderate |
| Comp. Ex. 3 | 4 | None | n-Octadecane (11.1 gsm) | None | None |
| Comp. Ex. 2 | 3 | Hydrophilic (12.5 gsm) | None | None | None |
| Example 1 | 4 | Hydrophilic (11.8 gsm) | n-Octadecane (11.1 gsm) | None | None |

Build-up and staining of the cartons were observed for Comparative Examples 4 and 5, but not for Comparative Examples 2 and 3 or Example 1. The build-up is clearly a problem for the comparative examples with outer layers containing hydrophobic lotion treatments. This may be the result of the direct interaction of the treatment with the carton or the interaction of the phase change material with the hydrophobic treatment and the carton. At 55° C. the phase change material is melted and free to mix with the softened hydrophobic treatment composition. In the case of the outer layer with hydrophilic lotion treatment (Example 1), the phase change material and the treatment are immiscible so the phase change material is presumably contained within the structure. Neither the hydrophilic treatment (Comparative Example 2) nor the phase change materials alone (Comparative Example 3) caused build-up in the cartons.

Example 2

An alternative four-ply structure can be created by applying a different treatment to each side of a two-ply web and then combining two of these webs. The resulting four-ply structure would then have hydrophilic lotion treated outer plies with a phase change material treated inner core.

Unlike Example 1, the hydrophilic treatment is separated from the phase change material on both sides by two layers of tissue instead of one. In this structure the hydrophilic treatment and two layers of tissue would serve as a potential barrier between the phase change material and human skin during use.

Two two-ply creped tissue sheets having a finished basis weight of 30 gsm consisting of 70 percent hardwood and 30 percent softwood fibers were used. Each ply was made from a stratified fiber furnish including two outer layers and a middle layer. Stearyl heptanoate was melted and placed in one cavity of a heated, dual offset gravure printing process equipped with an 8 BCM gravure roll. The Hydrophilic treatment composition from Comparative Example 2 was prepared and placed in the other cavity of the printing process equipped with a 4 BCM gravure roll. Both compositions were heated to a temperature of 63° C. and printed on opposite outer sides of each of the two-ply tissue products via a simultaneous offset rotogravure printing process. The fluid reservoirs of the printer were heated to 63° C. to insure the hydrophilic lotion treatment composition remained molten throughout the application process. The gravure rolls were electronically engraved, chrome-over-copper rolls supplied by Southern Graphics Systems (Louisville, Ky.). The rolls had a line screen of 360 cells per lineal inch. The rubber backing offset applicator rolls had a 75 Shore A durometer cast polyurethane surface and were supplied by American Roller Company (Union Grove, Wis.). The process was set up to a condition having 0.3125 inch interference between the gravure rolls and the rubber backing rolls and 0.003 inch clearance between the facing rubber backing rolls. The simultaneous offset/offset gravure printer was run at 150 feet/minute.

The treated webs were cooled to 25° C. to solidify the treatments before winding. The treated rolls were immediately treated a second time. Care was taken to ensure that the second printing pass applied the same treatment to a given side as was applied in the first pass.

The two two-ply treated rolls were combined and converted into four-ply finished product. The rolls were positioned on two unwinds so that the stearyl heptanoate treated plies of each roll would be in the center of the four-ply sheet, and the hydrophilic treated plies of each roll would be the outer plies of the four-ply sheet. The combined four-ply structure was calendared, crimped, and slit to standard facial tissue width. Example 2 was found to be cooling while causing little redness or skin damage.

Example 3

Example 3 was produced the same way as described in Example 2, but with a different hydrophilic lotion composition. The composition of the Hydrophilic Lotion Treatment Composition 2 is shown below in Table 2.

TABLE 5

| Hydrophilic Lotion Treatment Composition 2 | |
| --- | --- |
| Ingredient | Wt. % |
| Glycerin | 45% |
| Propylene Glycol | 50% |
| Sodium Stearate | 5% |

Example 3 was found to be cooling while causing little redness or skin damage.

These and other modifications and variations to the appended claims may be practiced by those of ordinary skill in the art, without departing from the spirit and scope of the appended claims. In addition, it should be understood that aspects of the various embodiments may be interchanged both in whole and in part. Furthermore, those of ordinary skill in the art will appreciate that the foregoing description is by way of example only, and is not intended to limit the appended claims.

What is claimed:

1. A dry substrate comprising:
   a first web comprised of fibers and a second web comprised of fibers, the first web and the second web each having a basis weight of from about 5 to about 60 grams per square meter;
   a temperature change composition located between the first web and the second web, the temperature change composition containing a phase change agent that undergoes a phase change at a temperature from about 20° C. to about 35° C., the phase change agent having a heat of fusion of at least about 100 J/g and being present on the dry substrate such that the dry substrate has a heat absorption factor of at least about 500 J/m$^2$; and
   a hydrophilic lotion on an exterior surface of the dry substrate comprising a carrier present in an amount between about 1% by the weight of the hydrophilic lotion composition and about 99.9% by the weight of the hydrophilic lotion composition and a thermo-reversible gelling agent present in an amount between about 0.1% by the weight of the hydrophilic lotion composition and about 50% by the weight of the hydrophilic lotion composition.

2. The dry substrate of claim 1 wherein the phase change agent is oil soluble and hydrophobic.

3. The dry substrate of claim 1 wherein the phase change agent is selected from the group consisting of tricaprin, parrafin, nonadecane, octadecane, stearyl heptanoate, lauryl lactate, lauryl alcohol, capric acid, cetyl babassuate, dipropylene glycol isoceteth-20 acetate, PEG-12, bis-PEG-15 methyl ether dimethicone, butyrospermum parkii butter, Di-$C_{12-15}$ alkyl fumarate, stearyl caprylate, cetyl lactate, cetyl acetate, $C_{24-28}$ alkyl methicone, glyceryl dilaurate, coceth-10, stearamidopropyl PG-dimonium chloride phosphate, cetyl alcohol, jojoba esters, and combinations thereof.

4. The dry substrate of claim 1 wherein the phase change agent has a heat of fusion of at least about 100 J/g.

5. The dry substrate of claim 1 wherein the carrier is selected from the group consisting of water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof.

6. The dry substrate as defined in claim 1 wherein the thermo-reversing gelling agent is selected from the group consisting of polyethylene glycols and derivatives thereof, PEG-150 pentaerythrityl tetrastearate, disteareth-75 IPDI, disteareth-100 IPDI, fatty alcohols, fatty acids, salts of fatty acids, and combinations thereof.

7. The dry substrate as defined in claim 1, wherein the temperature change composition is present on the web in an amount from about 4 gsm to about 40 gsm.

8. The dry substrate as defined in claim 1, wherein the substrate further comprises a third web, the third web having a basis weight of from about 5 to about 60 grams per square meter.

9. The dry substrate as defined in claim 1, wherein the phase change agent comprises a hydrocarbon, a wax, an oil, a fatty acid, a fatty acid ester, a dibasic acid, a dibasic ester, a 1-halide, a primary alcohol, an aromatic compound, an anhydride, an ethylene carbonate, a polyhydric alcohol, or mixtures thereof.

10. The dry substrate as defined in claim 1, wherein the substrate comprises a facial tissue.

11. The dry substrate of claim 1, wherein the first web comprises two plies and wherein the second web comprises two plies.

* * * * *